United States Patent [19]

Searle et al.

[11] 4,249,936

[45] Feb. 10, 1981

[54] ESTERS OF 2-CARBOXY-3-AZABICYCLO-(3.1.0)HEX-2-ENE

[75] Inventors: Robert J. G. Searle; Janet A. Day, both of Sittingbourne, England

[73] Assignee: Shell Oil Company, Houston, Tex.

[21] Appl. No.: 101,992

[22] Filed: Dec. 7, 1979

[30] Foreign Application Priority Data

Dec. 14, 1978 [GB] United Kingdom ............... 48489/78
Mar. 12, 1979 [GB] United Kingdom ............... 08615/79

[51] Int. Cl.³ .................... A01N 43/38; C07D 209/52
[52] U.S. Cl. .................................... 71/95; 260/326.27
[58] Field of Search ....................... 71/95; 260/326.27

[56] References Cited

U.S. PATENT DOCUMENTS

| 4,047,930 | 9/1977 | Kerr | 71/95 |
| 4,183,857 | 1/1980 | Kollmeyer | 260/326.5 B |

*Primary Examiner*—Catherine L. Mills

[57] ABSTRACT

Esters of 2-carboxy-3-azabicyclo(3.1.0)hex-2-ene, useful as intermediates to the cis-racemate of methanoproline, and as inhibitors of pollen formation in cereal grains.

7 Claims, No Drawings

ESTERS OF 2-CARBOXY-3-AZABICYCLO-(3.1.0)HEX-2-ENE

BACKGROUND OF THE INVENTION

3-Azabicyclo(3.1.0)hexane-2-carboxylic acid, also known as methanoproline, and certain of its esters, are known to inhibit (suppress) pollen formation in cereal grains: U.S. Pat. No. 4,047,930 (the acid being designated therein as 2-carboxy-3,4-methanopyrrolidine). Methanoproline exists in the forms of two geometric (i.e., cis and trans) isomers. Each of these isomeric forms exists in the forms of optical isomers. The racemic mixtures of both of the geometric isomeric forms inhibit pollen formation in cereal grains. However, it has been found that with respect to some cereal grains the cis racemate is more active for that purpose than is the trans racemate. Accordingly, it is desirable that there be available an effective method for preparing the cis racemate of methanoproline. Known methods for preparing it result in the formation of substantial amounts of the trans racemate.

DESCRIPTION OF THE INVENTION

A method for converting the trans racemate of methanoproline to the cis racemate now has been found.

According to this discovery, the trans racemate of methanoproline is esterified, the ester is dehydrogenated to the corresponding ester of 2-carboxy-3-azabicyclo(3.1.0)hex-2-ene, that ester is hydrogenated, and the resulting cis racemate of the ester is hydrolyzed to give the cis racemate of methanoproline.

By trans isomer is meant the geometric isomer in which the $-CO_2-$ group in the 2-position of the 3-azabicyclohexane ring is trans in configuration to the bridging group in the 6-position, and the cis isomer is the geometric isomer in which the $-CO_2-$ group is cis in configuration to the bridging group.

It should be noted that for each such geometric isomer, a pair of optical isomers exists, due to the asymmetry of the 2-carbon atom, resulting in the cis- and trans-racemic mixtures.

To simplify this disclosure, avoiding unnecessary repetition, the cis- and trans- racemates will hereinafter be designated as simply the appropriate cis and trans compounds.

The ester starting material can be the trans ester alone, or in any admixture with the cis ester, the product of the process provided by this invention being a mixture significantly enriched in the cis isomeric form, to the extent that in some cases the conversion is essentially complete.

The starting ester may, for example, be an alkyl, alkenyl, alkynyl, aryl or aralkyl ester in which the ester moiety may be unsubstituted or substituted by one or more of the same or different substituents selected from halogen, alkyl and alkoxy. Preferably, the ester is an alkyl, alkenyl or aralkyl ester in which the ester moiety is unsubstituted. More preferably, the ester is an alkyl ester having from 1 to 10, especially 1 to 4 carbon atoms in the alkyl group, or a benzyl ester. For example, the ester may be a methyl, ethyl, isopropyl or benzyl ester.

A method for preparing methanoproline is described in application Ser. No. 922,407 (K-3229). Esters of methanoproline, so produced, can be prepared by conventional procedures.

Conversion of the starting ester to the ester of 2-carboxy-3-azabicyclo(3.1.0)hex-2-ene can be carried out directly using an oxidizing agent. Manganese dioxide is a suitable reagent, and the oxidation can be performed simply by stirring the starting ester with manganese dioxide in the presence of a suitable solvent, for example, a hydrocarbon such as benzene or a light petroleum fraction. The reaction is conveniently performed at room temperature.

Alternatively, the conversion may be carried out indirectly, for example, by chlorinating or brominating the starting ester to give the N-chloro or N-bromo ester, and dehydrohalogenating the N-halo ester. The halogenation may be carried out using any suitable halogenating agent, for example, N-bromo- or, especially, N-chlorosuccinimide, or an organic or inorganic hypohalite, for example, t-butyl hypochlorite or sodium hypochlorite. Sodium hypochlorite may conveniently be used in the form of sodium hydroxide plus chlorine. The halogenation is suitably carried out by admixing the halogenating agent with the starting ester. Any suitable solvent, for example, an ether, may be used. The reaction may, for example, be carried out at a temperature in the range of from $-10°$ C. to $+30°$ C., the optimum temperature depending on the halogenating agent used. For example, if a hypohalite is used as halogenating agent, the reaction is preferably carried out at a temperature in the range of from $-10°$ C. to $+5°$ C., whereas if N-chlorosuccinimide is used as halogenating agent, the reaction is most conveniently carried out at room temperature.

Suitable dehydrohalogenating agents for the dehydrohalogenation step include organic bases and inorganic bases, for example, an alkali metal hydroxide or alkoxide. Care should be taken, however, to ensure tht the reaction conditions are such that the ester group is not attacked. For this reason, the base used should be relatively non-nucleophilic; for example, sodium ethoxide is generally preferred to sodium hydroxide. The reaction may be carried out in any suitable polar solvent, for example, an ether or an alcohol, and is preferably carried out at a temperature of up to $150°$ C., preferably at a temperature in the range $0°$ to $80°$ C.

The resulting azabicyclohexene ester may be isolated by any suitable method, or at least part of the reaction mixture containing the azabicyclohexene derivative may be used directly in the subsequent hydrogenation step.

The hydrogenation step of the process according to the invention may, for example, be carried out by using a hydride transfer agent. Preferably, however, it is carried out using gaseous hydrogen in the presence of a homogeneous or, preferably, heterogeneous catalyst, for example, a palladium or platinum catalyst, such as palladium charcoal or, preferably, pre-reduced platinum oxide. The process may be carried out at atmospheric pressure but it is preferably carried out at elevated pressure, for example, up to 150 atmospheres gauge.

The hydrogenation reaction is preferably carried out at room temperature. It may, however if desired, be carried out at elevated temperature, for example, up to $100°$ C.

If the alcohol from which the ester starting material is derived is a liquid, the hydrogenation reaction is preferably carried out using this alcohol as solvent. Thus, in one embodiment of the process, an ethyl ester is used as starting material and the hydrogenation is carried out using ethanol as solvent. However, any other suitable solvent may be used if desired—for example, an ester, such as ethyl acetate, or an aromatic hydrocarbon, such as toluene. If the ester starting material is itself a liquid, the reaction may be carried out without the use of a solvent.

If desired, the product obtained directly from the hydrogenation process, if it is an ester, can be converted into methanoproline or a salt thereof. This may be performed by any suitable method, for example, hydrolysis under acidic or basic conditions, and if desired subsequent conversion of the resulting free acid into a salt thereof, or conversion of a resulting salt into the corresponding free acid. Hydrogenation of certain esters may produce the cis methanoproline directly, if the starting ester moiety is one which is cleaved by hydrogenolysis. Thus, if the desired product of the process of the invention is methanoproline, a preferred embodiment of the process comprises starting from such an ester, preferably the benzyl ester. Hydrogenolysis of the benzyl ester leads not only to hydrogenolysis of the C=N double bond giving a cis isomer, but also leads to cleavage of the ester moiety. Thus, methanoproline is obtained directly. The starting ester may, if desired, be prepared by esterification of the free acid or a salt thereof. Thus, the process according to the invention may in effect be used to convert the trans isomer methanoproline or a salt thereof, into the cis isomer of such an acid, or a salt or an ester thereof.

The following examples describe particular instances of the application of the process of the invention, as well as exemplary esters of 2-carboxy-3-azabicyclo(3.1.0)hex-2-ene.

EXAMPLE 1

(a) N-chlorination of trans 2-ethoxycarbonyl-3-azabicyclo(3.1.0)hexane 3.24 g of tert-butyl hypochlorite was added dropwise to a stirred and ice-cooled solution of 4.65 g of trans 2-ethoxycarbonyl-3-azabicyclo(3.1.0)hexane in 90 ml of dry ethyl ether, under a nitrogen atmosphere and with the exclusion of light. The temperature rose from 0° to 10° C. The solution was stirred for 5 minutes.

(b) Preparation of 2-ethoxycarbonyl-3-azabicyclo(3.1.0)-hex-2-ene 0.69 g of sodium was dissolved in 90 ml of ethanol and the resulting solution was added quickly to the solution of 2-ethoxycarbonyl-3-chloro-3-azabicyclo(3.1.0)hexane obtained in (a) above. An exothermic reaction ensued, and the mixture was stirred and cooled for 30 minutes. A fine white precipitate which could not be filtered was produced. The solvent was evaporated off and the residue was taken up in ether, washed twice with water and dried over sodium sulfate. On evaporation, 4.8 g of 2-ethoxycarbonyl-3-azabicylo(3.1.0)hex-2-ene was obtained as an oil, b.p. (0.5 Torr.): 63°–65° C. The identity of the product was confirmed by NMR and IR spectral analyses.

(c) Preparation of cis 2-ethoxycarbonyl-3-azabicyclo(3.1.0)-hexane 1.0 g of Adams catalyst, consisting of platinum oxide, was added to 20 ml of ethanol and shaken under hydrogen at a pressue of 2 atmospheres gauge for 15 minutes, to reduce it to platinum prior to use. A solution of 1.5 g of 2-ethoxycarbonyl-2-azabicyclo(3.1.0)hex-2-ene in 20 ml of diethyl ether was added to the suspension of prereduced catalyst, and the mixture was shaken under hydrogen at 2 atmospheres gauge and at room temperature, for five hours. The mixture was filtered through "hyflo", a commercial filtering aid, and the solvent was removed by evaporation. 1.3 g of 2-ethoxycarbonyl-3-azabicyclo(3.1.0)hexane, as a pale yellow oil which crystallized on standing, was obtained. NMR spectrum analysis indicated that no trans isomer was present.

(d) Preparation of cis 2-carboxy-3-azabicyclo(3.1.0)hexane (methanoproline)

20 ml of 2 M sodium hydroxide was added to 1.2 g of cis 2-ethoxycarbonyl-3-azabicyclo(3.1.0)hexane and the suspension was stirred at room temperature for 1 hour, after which time the oil had all dissolved. The solution was stirred for a further 4 hours at room temperature and left to stand overnight. It was then passed through a column of Amberlite 410 resin in the OH$^-$ form. 1 liter of water and then 1 liter of 2 N hydrochloric acid were used as eluents. The resulting solvent was evaporated and the residue was applied to a column of Amberlite IRA 120 resin in the H$^+$ form, using water and then dilute ammonium hydroxide as eluents.

1 g of methanoproline product was obtained, shown by NMR spectrum analysis to be almost all in the cis isomeric form.

EXAMPLE 2

Preparation of 2-isopropoxy-3-azabicyclo(3.1.0)hex-2-ene

The procedure of Example 1 was repeated, except that 2-isopropoxycarbonyl-3-azabicyclo(3.1.0)hexane (92% trans isomer, 8% cis isomer) was used as starting material in step (a); potassium hydroxide dissolved in isopropyl alcohol was used as dehydrohalogenating agent in step (b); and a 5% palladium charcoal catalyst in isopropyl alcohol was used in step (c). The resulting product was 2-isopropoxycarbonyl-3-azabicyclo(3.1.0)hexane which was shown by NMR spectrum analysis to contain 85% cis isomer, 15% trans isomer. The product of step (b) was 2-isopropoxy-3-azabicyclo(3.1.0)hex-2-ene, a liquid, b.p. (0.4 Torr.): 64°–66° C. Its identity was confirmed by NMR and IR spectral analyses.

EXAMPLE 3

The procedure of Example 1 was repeated, except that the procedure of steps (a) and (b) combined were replaced by the following.

2 g of manganese dioxide was added to a solution of 1 g of 2-ethoxycarbonyl-3-azabicyclo(3.1.0) hexane in 50 ml of petrol, boiling point 40°–60° C. The resulting suspension was stirred at room temperature under a nitrogen atmosphere, and the reaction was monitored by gas-liquid chromatography. After 4 hours, a further 2 g of manganese dioxide was added.

The suspension was left overnight at room temperature, and then filtered and concentrated by evaporation. 0.85 g of solid 2-ethoxycarbonyl-3-azabicyclo(3.1.0)hex-2-ene was obtained.

EXAMPLE 4

The procedure of Example 2 was repeated except that steps (a) and (b) were replaced by the following.

A solution of 8.45 g of 2-isopropoxycarbonyl-3-azabicyclo(3.1.0) hexane in 100 ml of dry diethyl ether was added dropwise over 10 minutes to a stirred suspension of 11.48 g of N-chlorosuccinimide in 200 ml of dry diethyl ether, under nitrogen and protected from light.

The mixture was stirred at 25°–30° C. for 2½ hours. The mixture was then washed with brine (3×25 ml), dried over sodium sulfate, filtered, and cooled to 0° C. A solution of sodium isopropoxide (prepared by dissolving 1.15 g of sodium in 100 ml of dry isopropyl alcohol) and 100 ml of dry dichloromethane, was added dropwise at 0° C. under nitrogen, in the dark. The suspension was stirred at 0° C. for 1 hour, concentrated by evaporation and the residue was treated with 100 ml of water and 500 ml of diethyl ether. The ether solution was then dried over sodium sulfate, and the solvent was evaporated. 5.9 g of an orange liquid was obtained. This was distilled under vacuum under a nitrogen atmosphere. 2.7 g of 2-isopropoxycarbonyl-3-azabicyclo(3.1.0)hex-2-ene was obtained.

EXAMPLE 5

Preparation of 2-benzyloxycarbonyl-3-azabicyclo(3.1.0)-hex-2-ene (a) 1.84 g of tert-butyl hypochlorite was added dropwise to a solution of 3.69 g of the benzyl ester of 2-carboxy-3-azabicyclo(3.1.0)-hexane, containing 84% of trans isomer, in 70 ml of dry diethyl ether at 0° to 5° C. under nitrogen. The solution was stirred at 0° to 5° C., in the dark, for 15 minutes, then 5 ml of freshly-distilled triethylamine was added. The suspension was stirred at room temperature for 2 days, and was then concentrated by evaporation. The residue was shaken with 500 ml of diethyl ether and 25 ml of water, and the ether layer was separated, washed with 25 ml of water, dried over sodium sulfate and the solvent was evaporated. The residue was purified chromatographically to give 2.3 g of 2-benzyloxycarbonyl-3-azabicyclo(3.1.0)hex-2-ene. The identity of the product was confirmed by elemental analysis and IR spectrum analysis.

(b) A solution of 1.33 g of the unsaturated benzyl ester in 40 ml of absolute ethanol was added to a slurry of 0.65 g of 5% palladium charcoal in 10 ml of ethanol, under nitrogen. The mixture was then shaken under hydrogen at room temperature for 1½ hours. The mixture was filtered, and the aqueous ethanolic filtrate was evaporated to give a straw-colored glassy solid. NMR spectrum analysis showed that this solid was methanoproline, with a cis:trans ratio of 93:7.

EXAMPLE 6

Preparation of 2-methoxycarbonyl-3-azabicyclo(3.1.0)hex-2-ene

By a method analogous to that of Example 1, this compound was prepared from 2-methoxycarbonyl-3-azabicyclo(3.1.0)hexane. Sodium dissolved in methanol instead of ethanol was used as dehydrohalogenating agent. The desired compound was obtained as a straw-colored liquid in 70% yield. Its identity was confirmed by elemental analysis, and by NMR and IR analyses.

EXAMPLE 7

Prepartion of 2-allyloxycarbonyl-3-azabicyclo(3.1.0)hex-2-ene 2.17 g of tert-butyl hypochlorite was added dropwise to a stirred solution of 3.34 g of the allyl ester of 2-carboxy-3-azabicyclo(3.1.0)hexane in 90 ml of dry diethyl ether at 0° to 5° C. in the dark. The solution was stirred at 0° C. for 15 minutes, then 5 ml of dry, redistilled triethylamine was added. The suspension was stirred at room temperature for 3 days. It was then concentrated by evaporation, and the residue was shaken with 500 ml of diethyl ether and 20 ml of water. The ether layer was separated, dried over sulfate, filtered and the solvent was evaporated. The resulting oil was dissolved in a little ethyl acetate, and purified chromatographically.

1.7 g of the allyl ester was obtained. Its identity was confirmed by elemental analysis, and by NMR and IR spectral analyses.

Also, it has been found that the certain esters of 2-carboxy-3-azabicyclo(3.1.0)hex-2-ene significantly inhibit the formation of pollen in cereal grain plants. The active esters are those wherein the ester moiety is unsubstituted alkyl or alkenyl of up to seven carbon atoms, or is benzyl. Preferably, the ester moiety is alkyl of one to four carbon atoms. This invention accordingly includes the use of such esters for suppressing formation of pollen in cereal grain plants, and compositions adapted for that purpose containing the esters.

The esters inhibit (suppress) pollen formation, apparently by sterilizing the male anthers of small-grain cereal plants, without substantially affecting female fertility. This makes it possible to produce $F_1$ hybrids of self-pollinating plants using a simple chemical treatment. The invention therefore provides a pollen-inhibiting (suppressing) composition which comprises an ester of the acid of the formula I together with a suitable carrier.

The invention further provides a method of inhibiting (suppressing) pollen formation in a small-grain cereal plant, which comprises applying to the plant ester of 2-carboxy-3-azabicyclo(3.1.0)hex-2-ene, or a pollen-suppressing composition containing such an ester. The invention also provides a method of producing an $F_1$ hybrid seed which comprises cross-pollinating a plant which has been treated by the sterilizing process according to the invention with a second plant of a different strain.

Preferably, the active compound or composition is applied to a smal-grain cereal plant, for example, wheat or barley, when the plant is at a stage of growth between late tillering and emergence of the ear. The compound or composition is suitably applied at a dosage of active compound of from 0.05 to 2 kilograms per hectare, preferably at a dosage of from 0.25 to 1 kilogram per hectare.

A carrier in a composition according to the invention is any material with which the active ingredient is formulated to facilitate application to the plant to be treated, or to facilitate storage, transport or handling. A carrier may be a solid or a liquid, including a material which is normally gaseous but which has been compressed to form a liquid, and any of the carriers normally used in formulating herbicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3–10% w of a dispersing agent and, where necessary, 0–10% w of stabiliser(s) and/or other additives such as penetrants or stickers. Dusts are usually formulated as a dust concentrate having a similar compositions to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilisers, slow release modifiers and binding agents. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing insecticidal, herbicidal or fungicidal properties.

The pollen-inhibiting properties of esters of the invention were ascertained as follows:

Spring wheat, variety Sicco, was propagated in a glass-house in 13 centimeter pots containing a loam-based compost. Supplementary lighting was provided by high-pressure mercury vapor lamps to give a constant day length of 16 hours. The temperature was maintained at approximately 20° C.

The compound to be tested was formulated as an aqueous solution containing 0.1% Nonidet P 40 as wetting agent and 1% acetone to aid solubility. This formulation was diluted with water to various concentrations and sprayed onto plants to run-off. The plants were treated at the growth stage when the second node of the plant was just detectable.

At ear emergence but before anthesis, 5 heads from each treated pot were placed in cellophane bags to prevent cross-pollination. At maturity, the bagged ears were harvested, and seed set was recorded and compared with untreated controls.

The results are shown in the following Table.

TABLE

| Compound of Example No. | Dosage (ppm) | Grain Set Inhibition (% of control) |
|---|---|---|
| 1 | 200 | 42 |
| 2 | 200 | 7 |
|   | 1000 | 47 |
| 6 | 200 | 20 |
|   | 1000 | 61 |

It can be seen that all the test compounds produced a considerable reduction in seed set compared with the untreated control, clearly illustrating the ability of the compounds to sterilise the male anthers of the wheat.

I claim:

1. An ester of the formula

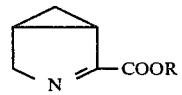

wherein R contains from 1 to 10 carbon atoms and is unsubstituted alkyl, alkenyl, alkynyl, phenyl or phenalkyl, or such substituted by one or more of halogen, alkyl and alkoxy.

2. An ester according to claim 1 wherein R is unsubstituted alkyl of 1 to 4 carbon atoms, allyl or benzyl.

3. An ester according to claim 2 wherein R is methyl, ethyl, isopropyl, allyl or benzyl.

4. A composition adapted for inhibiting pollen formation in cereal grain plants which comprises an ester of claim 1 wherein R is unsubstituted alkyl or alkenyl of up to 7 carbon atoms, or is benzyl, together with a carrier therefor.

5. A composition according to claim 4 wherein R is alkyl of from 1 to 4 carbon atoms.

6. A method of inhibiting formation of pollen in a cereal grain which comprises applying to a cereal grain plant an effective amount of a compound of claim 1 wherein R is unsubstituted alkyl or alkenyl of up to 7 carbon atoms, or is benzyl, or a composition of claim 4.

7. A method according to claim 6 wherein R is alkyl of from 1 to 4 carbon atoms.

* * * * *